US008790399B2

(12) United States Patent
Frazier et al.

(10) Patent No.: US 8,790,399 B2
(45) Date of Patent: Jul. 29, 2014

(54) TOTAL ARTIFICIAL HEART SYSTEM FOR AUTO-REGULATING FLOW AND PRESSURE BALANCE

(75) Inventors: Oscar H. Frazier, Houston, TX (US); William Cohn, Houston, TX (US)

(73) Assignee: Newheart Medical Devices, LLC, Houston, TX (US)

( * ) Notice: Subject to any disclaimer, the term of this patent is extended or adjusted under 35 U.S.C. 154(b) by 58 days.

(21) Appl. No.: 12/789,260

(22) Filed: May 27, 2010

(65) Prior Publication Data
US 2011/0098807 A1 Apr. 28, 2011

Related U.S. Application Data

(62) Division of application No. 11/244,836, filed on Oct. 6, 2005, now abandoned.

(51) Int. Cl.
A61M 1/12 (2006.01)
A61M 1/10 (2006.01)

(52) U.S. Cl.
CPC ............... A61M 1/10 (2013.01); A61M 1/1037 (2013.01)
USPC .......................................... 623/3.16; 623/3.1

(58) Field of Classification Search
CPC ..... A61M 1/10; A61M 1/101; A61M 1/1037; A61M 1/1046; A61M 1/1068; A61M 1/107
USPC ..................... 623/3.1–3.3; 606/213
See application file for complete search history.

(56) References Cited

U.S. PATENT DOCUMENTS

| | | | |
|---|---|---|---|
| 3,599,244 A | | 8/1971 | Wortman |
| 4,994,078 A | | 2/1991 | Jarvik |
| 5,049,134 A | * | 9/1991 | Golding et al. .............. 623/3.13 |
| 6,080,182 A | * | 6/2000 | Shaw et al. .................... 606/213 |
| 6,342,072 B1 | * | 1/2002 | Wartelle et al. ................ 623/3.2 |
| 6,540,658 B1 | | 4/2003 | Fasciano et al. |
| 6,926,662 B1 | * | 8/2005 | Aboul-Hosn et al. ......... 623/3.1 |
| 7,238,165 B2 | * | 7/2007 | Vincent et al. ............... 623/3.11 |
| 2005/0107658 A1 | | 5/2005 | Brockway |

FOREIGN PATENT DOCUMENTS

| | | |
|---|---|---|
| WO | WO88/05313 | 7/1988 |
| WO | WO00/37139 | 6/2000 |
| WO | WO2007/044601 | 4/2007 |

OTHER PUBLICATIONS

English translation of WO88/05313, Jul. 28, 1988, Lapeyre.

* cited by examiner

Primary Examiner — David Isabella
Assistant Examiner — Suba Ganesan
(74) Attorney, Agent, or Firm — Winstead PC

(57) ABSTRACT

The present invention provides a total artificial heart system for auto-regulating flow and pressure balance. In one embodiment the system comprises an atrial reservoir comprising inlets and outlets connectable to a mammalian cardiovascular system and at least first and second continuous pumps connected to the atrial reservoir. In further embodiments, the system comprises an atrial reservoir comprising at least two atrial chambers, and a means for transmitting fluid pressure between the atrial chambers. The means for transmitting fluid pressure include, but are not limited to a diaphragm, an interatrial window, a flexible membrane, a valve, a filter, or combinations thereof. In another embodiment, the means for transmitting fluid pressure comprises an implantable diaphragm comprising an outer rim attachable to biological tissue and a membrane anchored at its periphery by said outer rim.

11 Claims, 3 Drawing Sheets

TOTAL ARTIFICIAL HEART SYSTEM FOR AUTO-REGULATING FLOW AND PRESSURE BALANCE

CROSS-REFERENCE TO RELATED APPLICATIONS

This application is a divisional application of U.S. patent application Ser. No. 11/244,836, filed Oct. 6, 2005, which is incorporated by reference herein, in its entirety.

BACKGROUND

Over 50,000 people die each year because of congestive heart failure, a condition that often cannot be treated with drug or surgical therapies. Moreover, nearly 550,000 new patients are diagnosed with congestive heart failure each year. For most patients that suffer heart failure, the only option is heart transplantation via an organ donor or by artificial means. The scarcity of suitable donor hearts has left patients and doctors with no choice but to look to artificial heart therapies. Fortunately, great strides have been made in the development of ventricular assist devices (VADs). Instead of totally replacing heart function, a VAD augments the existing heart's ability to pump blood. These devices have saved many patients who would not have survived without a heart transplant. Despite it success, current VAD technology still has much room for improvement. The development of a viable long term total artificial heart replacement still remains the ultimate goal.

In the past, total artificial hearts (TAHs) have been based on a pulsatile system in an effort to mimic the human heart. However, such devices require prosthetic valves and external vent tubes. The prosthetic valves in pulsatile systems are prone to causing blood damage and blood clots while external vent tubes are a likely source for infection. Furthermore, current TAHs are still large, expensive to produce, and not anatomically suitable for implantation in small adults and children. In recent years, research has focused on continuous flow systems as an alternative to the traditional pulsatile model. In a continuous flow system, blood is continuously pumped through the body rather than pulsing the blood rhythmically as in the human heart.

Continuous flow systems offer several advantages over pulsatile systems. First, continuous flow pumps are generally smaller than pulsatile pumps. Shrinking the size of artificial heart devices will allow doctors to treat women and small children who previously were not candidates for pulsatile TAHs. Second, continuous flow pumps consume less energy than pulsatile systems. This property is important for quality of life issues, allowing the device to run on smaller batteries. Finally, continuous flow pumps have been developed that are magnetically driven with no mechanical bearings or valves, dramatically decreasing any chance of blood damage or long term failure.

Unfortunately, continuous flow pumps are not without drawbacks. The main problem with continuous flow pumps is their inability to auto-regulate or balance flow and pressure across the left and right side of the heart. Even in a healthy human heart, there is a 10 to 15 percent difference in flow and pressure between the left and right sides of the heart. This difference is because of the greater resistance in the systemic circulation i.e. the left side of the heart. In biventricular assist devices, where the patient's natural atria are utilized, an inability to auto-regulate flow and pressure may result in atrial collapse, a potentially fatal condition.

Prior attempts at overcoming this problem have utilized electronic monitoring and control for changing the pump speed. However, any solution involving electronic control systems will likely be unsuitable for long term patient survival due to the inherent limitations on the reliability and longevity of electronic sensors and control systems. Therefore, the ideal continuous flow system would contain a means to auto-regulate without the need for electronic control systems.

Consequently, there is a need for a simple system to auto-regulate flow and pressure balance in TAHs employing continuous flow pumps that may be used to temporarily or permanently replace a defective human heart.

BRIEF SUMMARY

The present invention provides a system for auto-regulating the flow and pressure balance in continuous flow TAHs. In the mammalian heart, the nervous system auto-regulates the flow and pressure balance across the left and right side of the heart in response to physiological changes in the body. However, current continuous flow TAHs do not have the benefit of the nervous system and must rely on electronic means to control flow and pressure. Not only is the longevity of such electronic systems a point of weakness, but the means by which they operate are often very complex. In order to avoid running wires through the patient's skin, researchers have moved toward employing wireless technology as a substitute, further complicating an already intricate device. The present invention accordingly provides a novel, simple approach to regulating flow and pressure balance by emulating the mammalian heart's Frank-Starling mechanism.

The Frank-Starling mechanism is the means by which the heart pumps harder when blood volume passing through it increases. The greater the blood volume in the heart, the more the cardiac muscles are stretched. Much like a rubber band, the heart exerts more force in pumping blood when it is filled with a greater volume. Therefore, in an embodiment comprising more than one atrial chamber, the system may comprise a means for transmitting fluid pressure between the left and right atria to auto-regulate flow and pressure balance in continuous flow TAHs with less need for electronic sensors.

In an additional embodiment, these and other needs in the art are addressed by a system comprising an atrial reservoir, said atrial reservoir comprising inlets and outlets connectable to a mammalian cardiovascular system, and at least first and second continuous pumps connected to said atrial reservoir. Moreover, the system may comprise at least first and second atrial chambers and a means for transmitting fluid pressure between first and second atrial chambers. In other embodiments, the atrial reservoir may comprise a single atrial chamber. The continuous flow pumps may then be connected to the pulmonary artery, the aorta, or both. The system may utilize any type of continuous flow pump including rotary axial flow pumps or rotary centrifugal pumps. The atrial reservoir preferably may mimic the Frank-Starling mechanism of the human heart. The size of the atrial reservoir is optimized to minimize blood damage and negative pressure conditions. The invention operates as a complete TAH system and requires substantially less electronic control for pressure and flow balance than the prior art.

Thus, the present invention comprises a combination of features and advantages that enable it to overcome the problems of prior devices. The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ".

The term "total artificial heart" (TAH) is used to describe any system, including any combination of synthetic and biological components, designed to be implanted in the body and to replace the natural functions of the human heart.

The term "continuous flow pump" is used to describe any pump which provides continuous and non-pulsatile flow.

The term "interatrial window" is used to describe an opening between the atrial chambers to allow fluid to pass through from one atrial chamber to another atrial chamber.

The term "auto-regulate" refers to the ability to regulate flow and pressure without the need for external sensors or controllers.

DETAILED DESCRIPTION OF THE PREFERRED EMBODIMENTS

Figure 1:
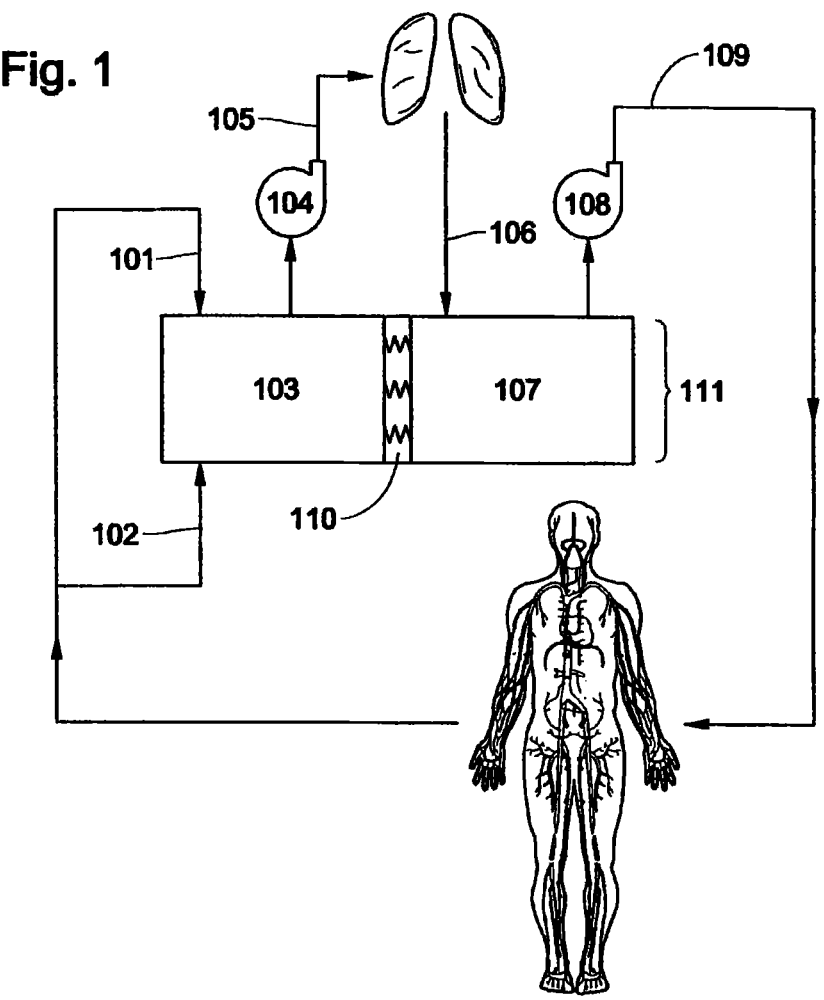
FIG. 1 gives a general schematic of the present invention.

FIG. 1 gives a general schematic of an embodiment of the invention. Oxygen-poor blood returning from the body enters an atrial reservoir 111 from the superior vena cava 101 and the inferior vena cava 102 into a first atrial chamber 103. According to one embodiment of the invention, a first atrial chamber 103 and a second atrial chamber 107 are separated by a means for transmitting fluid pressure 110. In alternative embodiments, the atrial reservoir 111 may comprise either a single atrial chamber or a plurality of atrial chambers. In further embodiments, the first atrial chamber 103 and second atrial chamber 107 may be detached from each other. The means for transmitting fluid pressure 110 may be constructed from a polymer or any other elastic material. Examples of suitable materials include without limitation elastomers, rubbers, latex, silicone, poly(isobutylene), or combinations thereof, or may take other forms, as discussed in detail below.

In certain embodiments, the means for transmitting fluid pressure 110 comprises an interatrial window to allow blood to pass from first atrial chamber 103 to second atrial chamber 107 and vice versa. The interatrial window may be large enough such that the first atrial chamber 103 and second atrial chamber 107 form a single atrial chamber. In other embodiments, the pressure transmitting means 110 includes a filter that allows blood to pass through, but filters material in the blood such as small blood clots. In another embodiment, the pressure transmitting means 110 comprises a valve that opens or closes in response to flow and pressure changes. In alternative embodiments, the pressure transmitting means 110 may comprise a combination of a valve and a filter. In yet further embodiments, the pressure transmitting means 110 may comprise an electronic control system, a pump, or combinations thereof. In all embodiments, pressure transmitting means 110 is non-thrombogenic and biocompatible.

Once inside first atrial chamber 103, the oxygen-poor blood is pumped out to the lungs through the pulmonary artery 105 by a first continuous flow pump 104. Oxygen-rich blood returns from the lungs via pulmonary vein 106 to second atrial chamber 107, from which it is pumped by a second continuous flow pump 108 through the aorta 109 to the rest of the body. Although continuous flow pumps 104, 108 are shown as rotary centrifugal pumps, any type of continuous flow pump may be used, including without limitation rotary axial flow pumps. The continuous flow pumps may further comprise pressure-sensitive impellers. Such impellers may comprise without limitation, angled vanes, curved vanes, flexible vanes, tapered vanes, round vanes, propellers, open impellers, closed impellers, or any combination thereof. The impellers may also comprise an optimal vane spacing to increase sensitivity to pressure. Without being limited by theory, it is believed that pressure-sensitive impellers may further augment the auto-regulation of flow and pressure balance in the artificial heart system. All veins and arteries may be connectable to the atrial reservoir through sutures or fittings.

While the invention provides a system to auto-regulate flow and pressure balance, it does not preclude electronic control of the continuous flow pumps. Thus, in some embodiments, the continuous flow pumps may be controlled by an electronic control system. In embodiments where the continuous flow pumps are electronically controlled, the pumps may be operated in either continuous or pulsatile mode.

Figure 2:
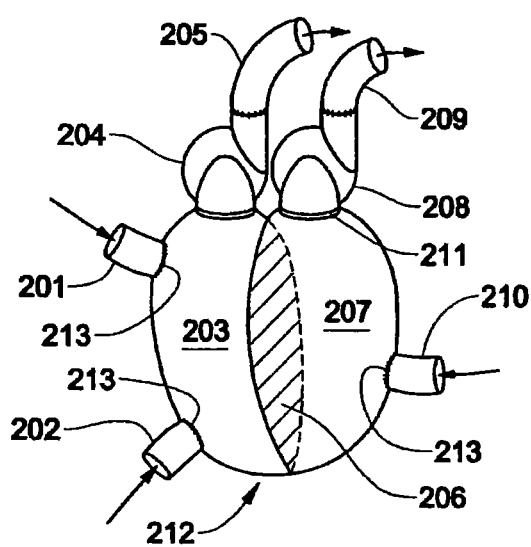
FIG. 2 illustrates an overall view of a preferred embodiment of the invention.

FIG. 2 is schematic diagram of one embodiment of the present invention. The superior 201 and inferior 202 vena cava are attached to an artificial atrial reservoir 212 via inlets 213. Artificial atrial reservoir 212 has inlets 213 for all necessary veins entering a normal heart. In this embodiment, the outer casing of atrial reservoir 212 may be a biocompatible, non-thrombogenic semi-rigid polymer. However, the outer casing may be constructed out of any biocompatible, non-thrombogenic material. Examples of suitable materials include without limitation polyurethaneurea, polytetrafluoroethylene, polyethylene, polycarbonate, silicone, or combinations thereof. The size and shape of artificial atrial reservoir 212 may be optimized to reduce blood damage and negative pressure conditions. In various embodiments, the artificial atrial reservoir 232 may comprise one or more atrial chambers. A first continuous flow pump 204 may be connected to the first atrial chamber 203 by a pump fitting 211. A second continuous flow pump 208 may be connected to the second atrial chamber 207 by a second pump fitting 211.

In another embodiment, the patient's own atria serve as an atrial reservoir 111. In this embodiment, the left and right ventricles of the patient's heart are excised, leaving a rim of ventricular tissue suitable for attaching the pump inputs. The inputs for first and second continuous flow pumps 104, 108 are connected to the patient's remaining right and left ventricular tissue, respectively. The output of first continuous flow pump 104 is connected to the pulmonary artery and the output of second continuous flow pump 108 is connected to the aorta. A pressure transmitting means 110 is created between the atria by excising the foramen ovale so as to form an interatrial window.

In certain embodiments (not shown), the interatrial window may be occupied by a diaphragm, which functions as pressure transmitting means 110. The diaphragm includes an outer rim suitable for attachment to tissue and a membrane anchored at its periphery to the outer rim. Preferably, the membrane is an elastic or elastomeric material that allows pressure or volume variations in one atrial chamber to be transmitted to the other atrial chamber. The membrane may comprise a polymer, but may be made from any suitable material. In other embodiments, the interatrial window may be left open to allow blood to pass from the right atrium to the left atrium in response to flow and pressure changes. Additionally, some embodiments may incorporate a flexible ring sutured to the existing tissue to keep the interatrial window open.

To further illustrate various illustrative embodiments of the present invention, the following example is provided.

Example

A preferred embodiment of the present invention as described above was implemented in a sheep model.

Materials and Methods

Centrifugal Pump

Figure 3:
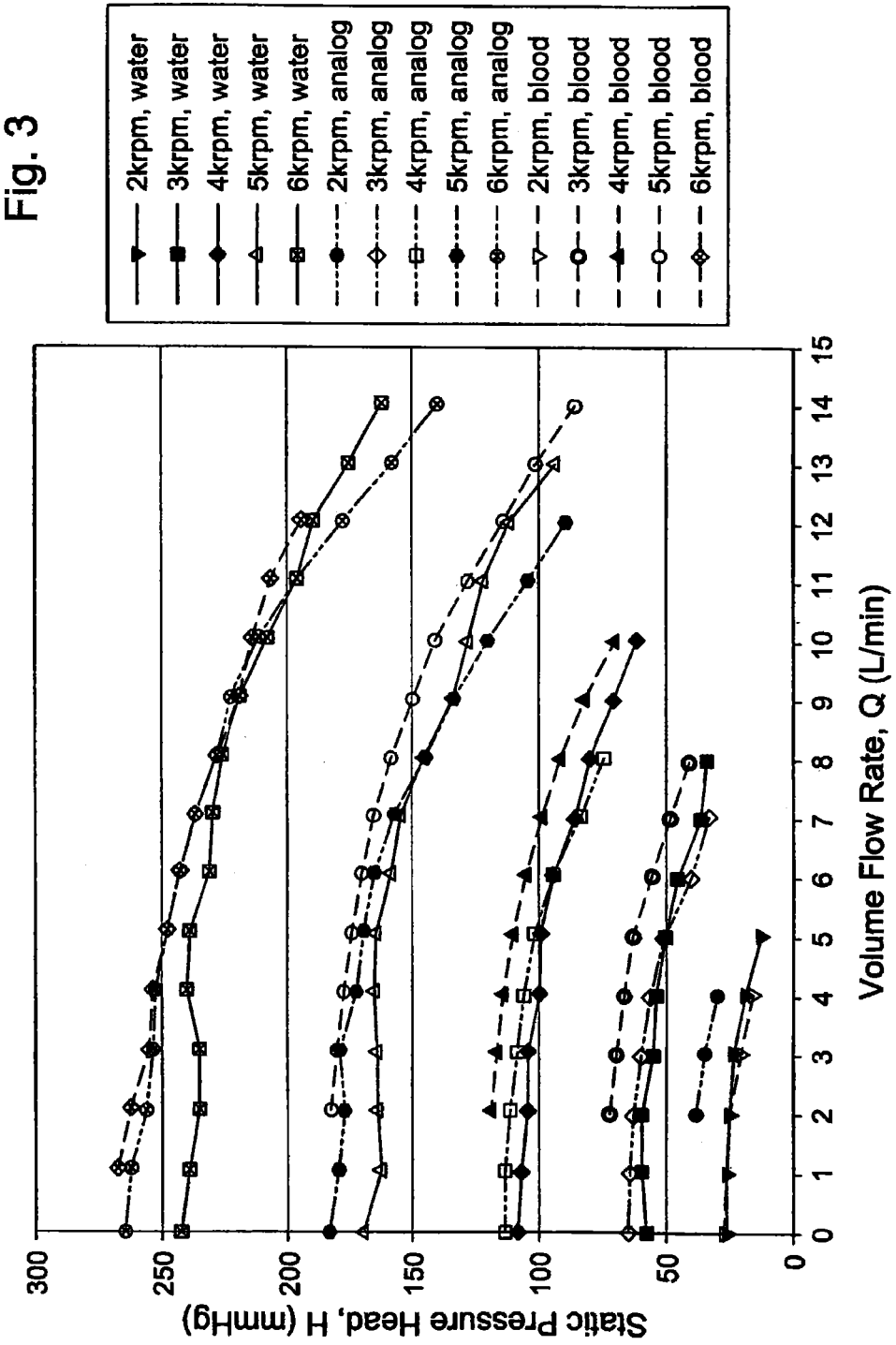
FIG. 3 is a plot of static pressure head (mmHg) versus volume flow rate (L/min) illustrating the Heartmate III's ability to generate 7 L of flow against 135 mmHg between 4500 rpm and 5000 rpm at its design point.

The Thoratec® HeartMate III is a compact, implantable, centrifugal VAD with a magnetically levitated rotor and no mechanical bearings. The steady-state pump pressure head-versus-volume flow rate (H-Q) characteristically shows that the pump can generate 7 L of flow against 135 mmHg between 4500 rpm and 5000 rpm at its design point (FIG. 3). The pump's design has been described in detail elsewhere.

Animal Model

A sheep weighing 59 kg was used in the study. The animal received humane care in compliance with the Principles of Laboratory Animal Care (National Society of Medical Research) and the Guide for the Care and Use of Laboratory Animals (National Institutes of Health publication No. 85-23, revised 1996).

Anesthesia and Surgical Preparation

A standard anesthesia protocol was followed. Food was withheld 12 hours before induction of anesthesia. The sheep was premedicated with glycopyrrolate (0.02 mg/kg) and xylazine (0.2 to 0.7 mg/kg) intramuscularly. A 12F triple-lumen venous catheter was inserted percutaneously into the right external jugular vein. Anesthesia was induced with intravenous ketamine (10 to 20 mg/kg). A cuffed endotracheal tube and an orogastric decompression tube were inserted. General anesthesia was maintained with isoflurane (1% to 3%) in oxygen (40% to 100%). The sheep was placed on the operating table in the right lateral decubitus position. Electrocardiographic leads were connected, and a rectal temperature probe was inserted.

Implantation

The left carotid artery and jugular vein were exposed for cardiopulmonary bypass (CPB) cannulation. A left thoracotomy was then performed in the fifth intercostal space, and the fifth rib was removed. Once the heart was exposed, heparin (3 mg/kg) was administered. A 17F cannula was placed in the left common carotid artery and connected to the arterial line of the heart-lung machine (Terumo SX-10 membrane oxygenator and Terumo roller pump; Terumo, Inc., Tokyo, Japan). After the superior and inferior vena cavas were selectively cannulated and were attached to the venous line with a Y connector, CPB was initiated. The aorta was cross-clamped and the body temperature cooled to 30° C.

The left and right ventricles were transected 1 cm below the atrioventricular (AV) groove, leaving a rim of ventricular tissue suitable for device attachment. The AV valves were excised, and the aorta and pulmonary artery (PA) were transected 1 cm above the ventriculo-arterial valves. A septal defect (1 $cm^2$) was created between the atria by excising the foramen ovale. The sewing rings of both atrial pumps were sutured to the corresponding atrial cuffs with 2-0 polypropylene sutures reinforced with TEFLON felt pledgets. Both pumps' inflow cannulas were inserted into the sewing rings of their respective atrial cuffs. The 16-mm Dacron outflow grafts were anastomosed in end-to-end fashion to the aorta and pulmonary artery, respectively, and were connected to the corresponding pumps. After the pumps and grafts were de-aired, both pumps were started. Once the body temperature was normalized (37.7 to 38.8° C.), the sheep was slowly weaned from CPB with the implanted dual pumps functioning as a total heart replacement system.

Intraoperative Hemodynamic Assessment

A pressure catheter was inserted via the left internal thoracic artery and was advanced proximally into the immediate vicinity of the aortic valve to measure the aortic pressure (AoP). Once surgery was completed, a pressure catheter was also placed in the common pulmonary artery to measure the pulmonary artery pressure (PAP). Two 16-mm ultrasonic flow probes (Transonics, Inc., Ithaca, N.Y.) were then placed on the right and left outflow grafts to measure the right ventricular assist device (RVAD) and LVAD outputs (QR and QL, respectively). The data were continuously recorded by a 16-channel computer data-acquisition system (Ponemah System, version 3.3; Gould Instrument Systems Inc., Valley View, Ohio).

The LVAD was operated at a constant speed of 4500 rpm. The RVAD speed was gradually increased from 2000 to 4500 rpm at 500-rpm intervals. The hemodynamic values were assessed for 10 minutes at each pump setting.

In the absence of directly measured right and left atrial pressures (RAPs and LAPs, respectively), these parameters were calculated from H-Q curves for known rpm, pump flow, and back pressure (PAP and AoP).

Echocardiographic Assessment

Serial 2-dimensional, transepicardial studies were done at each pump speed. Echocardiographic assessment was performed according to the guidelines of the American Society of Echocardiography with a Sonos 2000 ultrasound system (Hewlett-Packard, Palo Alto, Calif.), equipped with a 2.5-MHz phased-array transducer. Color Doppler echocardiography and injection of agitated saline contrast material into the right atrium were used to assess interatrial shunts at different pump settings.

Blood Gas Analysis

An 18-gauge angiocatheter was inserted into the right (pulmonary artery) and left (aortic) outflow grafts to draw blood samples. One sample was taken from each side, at each pump speed, to assess the oxygen saturation in the outflow grafts. A Novastat Profile M blood gas analyzer (Nova Biomedical Company, Waltham, Mass.) was used for blood gas analysis.

Operation of the Pump in Pulsatile Mode

After continuous-flow hemodynamic measurements were obtained, the pump was operated in pulsatile mode. The LVAD's mean rotational speed, amplitude of pulsatility, and pulse rate were programmed with an external personal computer to create pulsatile flow. Such flow was achieved by sharply alternating the rotor speed between 1500 rpm (artificial diastole) and 5500 rpm (artificial systole) at a rate of 80 artificial beats/min and a "systolic" interval of 50%. The LVAD's outflow ranged from 0 to 12.6 L/min (mean, 4.3 l/min), while the RVAD's outflow was maintained constantly at 5.5 L/min. A water-filled pigtail catheter was inserted via the left carotid artery and was advanced to the iliac bifurcation to measure the arterial pressure changes at that site, at the iliac bifurcation, and at the infrarenal, suprarenal, descending, and ascending aortic levels.

Results

Table 1 shows the effects of increased RVAD speed on the left and right pumps' outflow, mean PAP, AoP, RAP, LAP, interatrial shunt, oxygen saturation, and atrial collapse.

Figure 4:
FIG. 4 is a plot showing the pressure waveforms measured at different levels of the aorta when the left ventricular assist device was operating in pulsatile mode.

The LVAD also successfully created pulsatile circulation in the aorta. Pulse pressures ranged from 20 mmHg (with a pigtail catheter in the iliac bifurcation) to 55 mmHg (with a pigtail catheter in the ascending aorta). FIG. 4 shows the pressure waveforms measured at different levels of the thoracic and abdominal aorta when the LVAD was in pulsatile mode.

Discussion

The present case is the first in which dual centrifugal pumps were implanted for total heart replacement after biventricular excision and in which the native atria were used as inlet-cannula cuffs as well as atrial reservoirs for intrathoracic implantation of the pumps. In this fashion, the total systemic and pulmonary circulations were successfully taken over in the acute setting.

The left thoracotomy is an ideal approach for total heart replacement with dual centrifugal VADs in the ovine model. The atria, PA, and aorta are easily accessible with this approach, which allows rapid anastomosis of the right and left outflow grafts and sewing rings, followed by dual VAD implantation. Ventricular remnants provide enough tissue support for anastomosis of the sewing rings. Moreover, by

TABLE 1

Effects of Increased Right Ventricular Assist Device Speed on Left and Right Outflow-Graft Flow, Systemic and Pulmonary Pressures, Interatrial Shunting, Oxygen Saturation, and Atrial Collapse

| | RVAD/LVAD Speed (rpm) | | | | | |
|---|---|---|---|---|---|---|
| Variable | 2000/4800 | 2500/4500 | 3000/4500 | 3500/4500 | 4000/4500 | 4500/4500 |
| PA/Ao flows (L/min) | 2.8/10.6 | 3.8/8.9 | 5.0/84 | 8.3/9.8 | 9.6/10.0 | 10.9/9.0 |
| Pa/Ao pressures (mmHg) | 12/78 | 26/69 | 29/75 | 40/92 | 40/90 | 45/84 |
| RA/LA pressures (mmHg) | −21/−7 | −22/−51 | −36/−50 | −28/−28 | −30/−27 | −45/−33 |
| Interatrial shunt (ECHO) | R to L | R to L | R to L | BD | BD | BD |
| PA/Ao $O_2$ Saturation (%) | 83.4/87.1 | 89.8/94.8 | 94.9/96.5 | 97/99.6 | 96.7/99.6 | 97.7/99.6 |
| R/L Atrial Collapse | No | No | No | No | No | No |

Ao, aortic;
BD, bidirectional;
ECHO, echocardiographic;
L, left;
LA, left atrium;
LVAD, left ventricular assist device;
$O_2$, oxygen;
PA, pulmonary artery;
R, right; RA, right atrium;
RVAD, right ventricular assist device As the RVAD speed was increased, the PA/aortic flow (Qp/Qs) ratio increased from 0.26 and 0.15 at 2000 rpm to 1.21 and 0.53 at 4500 rpm. Higher RVAD speeds also resulted in an increased PA/aortic pressure ratio and a decreased right-to-left atrial shunt, which gradually became a left dominant bidirectional shunt.

The calculated right and left atrial pressures reflected the echocardiographic shunt directions, the shunt becoming bidirectional when the interatrial pressures equalized between the left and right sides.

The results of blood gas analysis in the outflow grafts were also consistent with the echocardiographic findings, showing a gradual increase in right-sided oxygen saturation at increased RVAD speeds.

At no pump speed did the atria collapse.

preserving the native atria, one can avoid using a prosthetic atrial cuff, which might have a long-term thrombogenic potential. Although the ovine model has some size limitations, the surgical technique can be easily adapted for the bovine model; alternatively, the size of the pump may be further reduced. Moreover, the sheep may be used to test the short- or long-term effects of completely non-pulsatile circulation on pulmonary and systemic perfusion.

In the present experiment, increasing the RVAD speed at a given LVAD setting resulted in higher PA flows and pressures, with little or no change in aortic flows and pressures. The interatrial window maintained a hemodynamic balance and kept the oxygen saturation in equilibrium between the left- and right-sided circulations without atrial collapse, even in the presence of mismatched LVAD and RVAD flows. At equal pump speeds, however, the PA flow exceeded the aortic flow.

A desirable balance was achieved by keeping the RVAD speed slightly lower than the LVAD speed. With the RVAD operating at 4000 rpm, pulmonary and systemic flows were almost equal (9.6 and 10.0 L/min, respectively), and PAP and AoP were acceptable even under such exaggerated high-flow conditions. The best hemodynamic results were observed, however, when the RVAD was operating at 3000 to 3500 rpm. This finding is consistent with previous evidence that the best hemodynamic results are achieved when LVAD flow is 30% higher than RVAD flow. Although in normal physiologic conditions the difference in flow rate is only 10-15%, the greater difference may be due to unaccounted variations in an artificial system.

The LVAD's relatively stiff speed control, low rotor mass, and magnetic rotor suspension cause the system to have low inertia. This characteristic enables very rapid speed changes that can be used to simulate a physiologic pulse. In our experiment, which was devoid of any native contractility, LVAD-induced aortic pulse pressures of 25 to 35 mmHg were measured as far distally as the iliac bifurcation. Significantly, the maximum rate of pressure increase (dP/dt) was 150 mmHg/s, which closely emulated physiologic values, although the energy equivalent pressure and mean arterial pressure were approximately equal. The option to use such an artificial pulse may be clinically beneficial for brief critical periods or for certain patients such as those with impaired renal function.

In conclusion, when implanted for total heart replacement, the dual continuous-flow centrifugal pumps successfully maintained the pulmonary and systemic circulation in our ovine model. Compared with the large, costly total artificial heart, dual continuous-flow pumps may offer a more practical, economical alternative for selected patients with end-stage heart failure. Moreover, experience with these pumps may allow researchers to design TAHs that are substantially smaller than current models and that are not affected by mechanical wear. This experiment showed the feasibility of biventricular replacement with dual continuous-flow pumps using an atrial communication to correct or offset the physiologic left- and right-atrial output imbalance while preserving satisfactory systemic oxygenation.

While preferred embodiments of this invention have been shown and described, modifications thereof can be made by one skilled in the art without departing from the scope or teaching of this invention. The embodiments described herein are exemplary only and are not limiting. Accordingly, the scope of protection is not limited to the embodiments described herein, but is only limited by the claims which follow, the scope of which shall include all equivalents of the subject matter of the claims.

What is claimed is:

1. An artificial heart system comprising:
    an artificial atrial reservoir of an artificial heart;
    said atrial reservoir comprising at least a first and second atrial chambers, wherein the first and second atrial chambers are artificial chambers;
    said atrial reservoir comprising inlets and outlets connectable to a mammalian cardiovascular system;
    at least first and second continuous flow pumps connected to said atrial reservoir;
    said first continuous flow pump connected to said first atrial chamber;
    said second continuous flow pump connected to said second atrial chamber; and
    an interatrial window positioned between the first and second atrial chambers, wherein the interatrial window allows blood to pass from the first atrial chamber to the second atrial chamber through the interatrial window, and the interatrial window allows fluid pressure to be transmitted from said first atrial chamber to second atrial chamber.

2. The artificial heart system of claim 1, further comprises a diaphragm occupying said interatrial window, wherein said diaphragm comprises:
    an outer rim positioned in the interatrial window; and
    a membrane anchored at its periphery to said outer rim, wherein the membrane allows blood to flow between the first and second atrial chambers.

3. The artificial heart system of claim 2, wherein said diaphragm comprises a polymer.

4. The artificial heart system of claim 2, wherein said membrane is a filter.

5. The artificial heart system of claim 2, wherein said diaphragm comprises an elastic material.

6. The artificial heart system of claim 1, wherein said interatrial window comprises a flexible ring.

7. An implantable diaphragm for auto-regulating flow and pressure balance in an artificial heart system comprising:
    an artificial atrial reservoir of an artificial heart providing a left and right artificial atria;
    an outer rim positioned in an interatrial window between said left and right artificial atria; and
    a membrane anchored at its periphery by said outer rim, wherein the membrane allows blood to pass from the left artificial atria to the right artificial atria through the interatrial window.

8. The implantable diaphragm of claim 7, wherein said membrane comprises a polymer.

9. The implantable diaphragm of claim 7, wherein said polymer comprises elastomer, rubber, latex, silicone, poly(isobutylene), or combinations thereof.

10. The implantable diaphragm of claim 7, wherein said membrane is a filter.

11. The implantable diaphragm of claim 7, wherein said membrane comprises an elastic material.

* * * * *